United States Patent [19]
Vander Heyden et al.

[11] Patent Number: 5,759,862
[45] Date of Patent: Jun. 2, 1998

[54] MEASURING HEATING VALUE USING CATALYTIC COMBUSTION

[75] Inventors: William H. Vander Heyden, Mequon, Wis.; Ronald Arthur Berg, Tulsa, Okla.

[73] Assignee: Badger Meter, Inc., Milwaukee, Wis.

[21] Appl. No.: 787,671

[22] Filed: Jan. 24, 1997

Related U.S. Application Data

[63] Continuation of Ser. No. 449,506, May 24, 1995, abandoned.

[51] Int. Cl.$^6$ ..................................................... G01N 7/14
[52] U.S. Cl. ........................... 436/147; 436/148; 436/152; 422/94
[58] Field of Search ............................... 436/147, 151, 436/152, 148; 422/94–98

[56] References Cited

U.S. PATENT DOCUMENTS

| | | |
|---|---|---|
| 3,777,562 | 12/1973 | Clingman, Jr. . |
| 4,062,236 | 12/1977 | Clingman, Jr. . |
| 4,125,018 | 11/1978 | Clingman, Jr. . |
| 4,125,123 | 11/1978 | Clingman, Jr. . |
| 4,285,245 | 8/1981 | Kennedy ................................ 73/861 |
| 4,614,721 | 9/1986 | Goldberg ............................ 436/147 |
| 5,012,432 | 4/1991 | Stetter et al. ....................... 364/557 |

FOREIGN PATENT DOCUMENTS 0 304 266  8/1988  European Pat. Off. .

*Primary Examiner*—Lyle A. Alexander
*Attorney, Agent, or Firm*—Quarles & Brady

[57] ABSTRACT

The heating value of a sample gas is calculated by a microcontroller from the heating value of a reference gas, and from flow ratios determined as the gas is consumed by catalytic combustion. The combustible gas is mixed with a combustion supporting gas, such as air, and flowed to a catalytic apparatus. In one embodiment, a molar flow meter is connected in the supply line for the combustible gas to measure the molar flow rate of a reference gas and a sample gas. Molar flow rates of the reference gas and the sample gas are determined at maximum temperature of combustion of the gas. In a preferred embodiment, a valve chamber is charged with a gas to a predetermined pressure and then discharged. During the discharge cycle, the apparatus senses the maximum temperature of combustion which corresponds to the point of optimum fuel-to-air ratio for catalytic combustion. Based on flow rates and the optimum fuel-to-air ratio, heating value of the sample gas is calculated by a microcomputer and output to a visual display or other output device.

21 Claims, 7 Drawing Sheets

MEASURING HEATING VALUE USING CATALYTIC COMBUSTION

This is a continuation of application Ser. No. 08/449,506 filed May 24, 1995, now abandoned.

BACKGROUND OF THE INVENTION

The field of the invention is methods and apparatus for determining the heating value of gases.

The measurement of the heating value of natural gas is important in controlling combustion and is a necessary measurement in the distribution and sale of natural gas. There are three commonly used methods for measuring heating value.

The first is the method of calorimetric measurement in which a volume of the gas is sampled and then completely combusted. An amount of heat is liberated by the complete combustion and is carefully measured and accumulated. The amount of heat liberated can be manifested by a change in temperature. The combustion may be by flame or by other methods not producing an open flame, such as by passing the gas over a catalytic material. In the case of catalytic combustion, the amount of heat liberated can be measured either by temperature changes related to the catalytic reaction, by changes in power supplied to heat the catalyst or by measuring the temperature of the catalytic material.

A second method for measuring heating value is constituent analysis. Using a chromatograph, the fraction of each chemical constituent in the gas is determined. Then, the heating value is determined by summing the heating value for the individual constituents.

The third method is stoichiometry, in which combustion is substantially complete. This type of combustion produces maximum flame temperature and minimum oxygen in the exhaust stream. In this case, natural gases are combusted with air and the fuel-to-air ratio is adjusted until combustion results in either a maximum flame temperature or the stoichiometric point of perfect combustion, i.e., the knife edge when there is no remaining oxygen.

Clingman, U.S. Pat. No. 3,777,562, is an example of the third method. In Clingman, heating value is measured by combustion of a gas with amounts of air that are adjusted to obtain the maximum flame temperature. This is further disclosed in Clingman, U.S. Pat. Nos. 4,062,236, 4,125,018 and 4,125,123. In each of these patents, the combustion of the air-gas mixture is accomplished with a combustion flame on a burner top and with a temperature sensing device such as a thermocouple.

Catalytic combustion or catalytic oxidation is a known phenomenon with hydrocarbons. A mixture of hydrocarbon gas and air in the presence of platinum and/or palladium material will produce an oxidation reaction. The reaction occurs at temperatures below a normal ignition temperature associated with the hydrocarbon. For example, methane when mixed with air, in a stoichiometric proportion, will ignite at a temperature of about 630° C. and reach an open flame temperature exceeding 1600° C. Catalytic oxidation can take place at catalyst temperatures as low as 400° C. although efficient catalysis is then achieved at a temperature near 500° C. Therefore, for methane-containing gaseous mixtures, catalytic oxidation is enabled below the ignition temperatures of the surrounding atmosphere.

In catalytic combustion practice, it is usual to mix the sample gas with a fixed amount of air, usually excess air, where the proportion of air is more than sufficient to provide all the oxygen required for oxidation of the sample gas.

In catalytic oxidation, the temperature of the catalyst must be limited to prevent overheating and runaway temperature and reaction conditions. The usual control methods are diffusion limiting and direct temperature control of the catalyst.

In diffusion limiting, the rate at which a mixed gas stream can contact the catalyst is limited by diffusion through a porous structure such as a ceramic bead. The diffusion process limits the contact and prevents a runaway reaction.

Another way to control the amount of mixed gas available for combustion is by measuring the temperature of the catalyst and adjusting the gas flow rate to maintain a certain temperature or narrow range of temperatures. Either method is acceptable for avoiding thermal runaway.

Goldberg, U.S. Pat. No. 4,614,721 and Stetter, U.S. Pat. No. 5,012,432, describe measurement of heating values using catalytic combustion. In Goldberg, the measurement of heating value requires measuring temperature before and after catalytic combustion to determine the heating value per unit volume of the gas. In Stetter, precise constant volumes of the gas are sampled and then oxidized using reaction with a catalyst to generate a signal representative of the heat released. A baseline signal is produced for air, and then a reference gas flow and a sample gas flow are reacted with the catalyst to provide further signals for comparison with the baseline signal.

SUMMARY OF THE INVENTION

The present invention modifies and improves the methods of stoichiometric or maximum flame temperature combustion of gases to measure heat content by employing a catalytic combustion process.

Such a process lowers the temperature of oxidation and combusts the gas without producing an open flame, thereby making the process suitable for operation in hazardous environments. The normal temperatures associated with catalytic combustion are lower than open flame combustion temperature and can be below the ignition temperature of certain hazardous environmental atmospheres.

The invention provides for the control of the air and fuel mixture in response to the temperature of the catalytic reaction. The peaking of combustion temperature at the proper proportion does not require a set operating temperature on the catalyst itself. The only requirement is that a peak response be determined by proportional mixing of the fuel and the air.

In the present invention, the reference gas is mixed with a proportion of air. The mixed gas flow is directed over or through a catalytic bed or bead, where the fuel is oxidized. The temperature is measured by appropriate sensors and the fuel-to-air ratio is varied until the oxidation temperature reaches a substantial maximum value. Under stoichiometric conditions, this is the fuel-to-air ratio that just extinguishes the presence of oxygen in the exhaust gas stream.

Only at that balance of air and fuel where the air and fuel are properly proportioned is the maximum energy released and a peak temperature reached.

In one embodiment, this is accomplished by positively controlling flow rates and measuring the flow rates of a sample gas and a reference gas at peak temperature. Heating value for a sample gas can then be calculated with reference to pre-stored values for the heating value of the reference gas.

In a second embodiment, the fuel-to-air mixture is varied by allowing pressure in a volume chamber to decay to produce a decreasing flow of fuel which leans out the fuel-to-air mixture. Again flow rates are measured for a sample gas and a reference gas at peak temperature of catalytic combustion. Heating value for a sample gas can then be calculated with reference to pre-stored values for the heating value of the reference gas.

Although the invention preferably uses a temperature sensor for sensing the stoichiometric point of combustion, such point could also be determined by monitoring a minimum amount of oxygen in the exhaust from the combustion process, thereby signifying substantially complete combustion.

Various objects and advantages will be apparent to those of ordinary skill in the art from the description of the preferred embodiment which follows. In the description, reference is made to the accompanying drawings, which form a part hereof, and which illustrate examples of the invention. Such examples, however, are not exhaustive of the various embodiments of the invention, and, therefore, reference is made to the claims which follow the description for determining the scope of the invention.

DESCRIPTION OF THE PREFERRED EMBODIMENT AND AN ALTERNATIVE EMBODIMENT OF THE INVENTION

Figure 1:
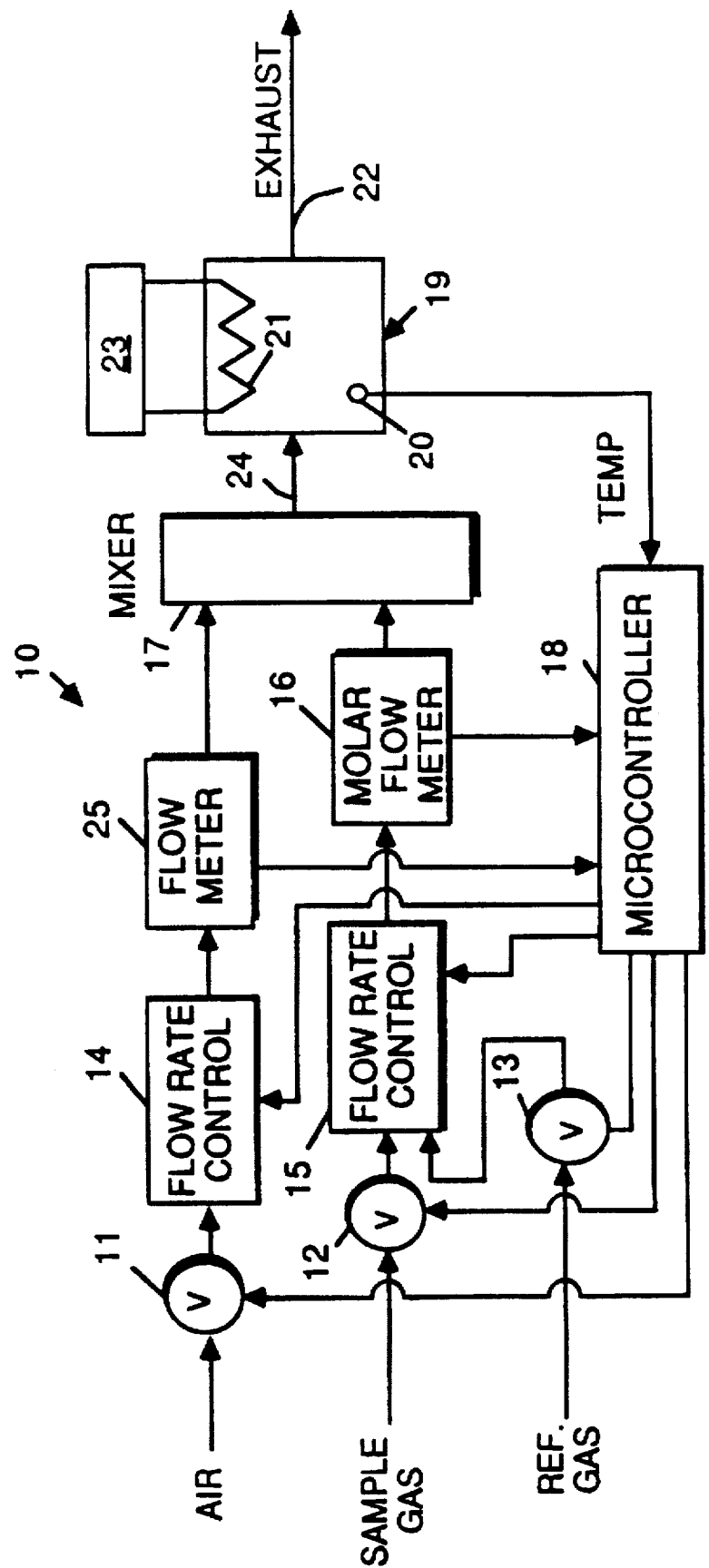
FIG. 1 is a schematic diagram of an apparatus for practicing the method of the present invention.

Referring to FIG. 1, an alternative embodiment of the invention will be described first, to be followed by a simplified preferred embodiment of the invention. The apparatus that is represented generally by reference 10. The apparatus supplies a mixture of air and combustible gas through mixer 17 to a catalytic heater apparatus represented generally by reference 19.

Catalytic heater apparatus 19 includes heater element 21 for heating the catalytic material to a temperature of 400° C. or more. Heater element 19 is energized by electricity from a power source 23. Temperature sensor 20 is embedded in the catalytic material to sense the temperature at the reaction surface of the catalytic material. Temperature sensor 20 generates a signal to an input on microcontroller 18. This signal is recognized by the microcontroller 18 as representative of temperature. From catalytic device 19, an exhaust stream 22 is exhausted. This exhaust stream 22 includes air, the products of combustion and any unburned gas. Additional steps may be taken to process the exhaust stream.

Microcontroller 18 is a suitable microelectronic CPU (central processing unit) with built-in A-to-D and D-to-A interface circuitry. Microcontroller 18 operates by executing program instructions, some of which are represented by blocks in the flow chart in FIGS. 2a and 2b, the instructions being stored in a memory also represented generally by reference 18.

Apparatus 10 more particularly includes on-off valves 11, 12 and 13 for allowing the flow of air, sample gas and reference gas, respectively, to mixer 17. The actual rate of flow is commanded through flow rate control devices 14, 15 of a type known in the art, in which input signals in the 4–20 milliamp range are sent to the devices 14, 15, to control the output flow of gas from the devices 14, 15. Device 15 is connected first to the reference gas and then to the sample gas by operation of on-off valves 12, 13.

Flow meter 25 is connected in the air line to sense the rate of flow of air and to provide an input signal to the microcontroller 18. Similarly, flow meter 16 is connected in the gas line to sense the rate of flow of gas and to provide an input signal to the microcontroller 18. It should be noted that flow meter 16 is preferably a molar flow meter of the type disclosed in Kennedy, U.S. Pat. No. 4,285,245 for sensing molar flow rate in response to pressure drops from the flow of gas out of a chamber. Such a flow meter is incorporated in a product commercially offered by the assignee under the trade designation "TRU-THERM".

The apparatus 10 in FIG. 1 establishes a closed control loop in which microcontroller 18 senses actual air flow rate and compares it to an internal command to adjust the air flow rate signal to device 14. The apparatus 10 also establishes a closed control loop in which microcontroller 18 senses flow rate of the gas consumed by combustion. The microcontroller 18 compares this flow rate to an internal command, and then adjusts the output signal to device 15.

The gas and air streams from devices 14 and 15 flow into the mixer 17. There, the gas and air streams are mixed thoroughly and the mixed stream flows to the catalytic bed in device 19 through conduit 24.

The flow meter 16 in the gas stream should be a molar flow meter of the type disclosed in Kennedy, U.S. Pat. No. 4,285,245. This eliminates the molecular weight of the gas from consideration in gas measurements. It is not necessary that the flow meter 12 in the air stream be a molar flow meter, because the molecular weight of air based on typical constituent gases is known.

The process of mixing, adjusting and finding the fuel/air mixture which produces a maximum temperature is performed for the reference gas and then the sample gas. The molar flow rate of the reference gas and the sample gas are then compared to determine the heating value. Assuming the temperature is constant during the sample and reference cycle, the sample gas heating value is calculated as:

$$H_{sample} = H_{ref} \left( \frac{\dot{n}_{ref}}{\dot{n}_{sample}} \right) \left( \frac{\omega_{air\ sample}}{\omega_{air\ ref}} \right) \quad (1)$$

where $H_{ref}$ is the heating value of the reference gas, $H_{sample}$ is the heating value of the sample gas, $\dot{n}_{ref}$ is the molar flow rate of the reference gas and $\dot{n}_{sample}$ is the molar flow rate of the sample gas, $\omega_{air\ ref}$ is the mass flow rate of air in the reference flow stream, and $\omega_{air\ sample}$ is the mass flow rate of air in the sample flow stream. The ratio of $\dot{n}_{ref}$ to $\omega_{air\ ref}$ represents the fuel-to-air ratio in the reference gas flow stream. The ratio of $\dot{n}_{sample}$ to $\omega_{air\ sample}$ represents the fuel-to-air ratio in the sample gas flow stream. Equation 1 thus demonstrates that the ratio of the two foregoing ratios is multiplied by the heating value of the reference gas $H_{ref}$ to obtain the heating value of the sample gas.

Using the apparatus of FIG. 1, the sample gas is disconnected and a reference gas is introduced by closing valve 12 and opening valve 13. A reference gas, such as methane, is flowed through apparatus 15, 16 is mixed in apparatus 17, and the mixture flows into the catalytic apparatus 19. The ratio of gases in the mixture of air and the reference gas is regulated until the temperature of the catalytic combustion is at a substantially maximum temperature. This can be accomplished by regulating the flow of air or regulating the flow of the reference gas.

It is generally preferred that the mass flow rate of the reference gas be varied, because the ratio of air to reference gas may be in the range from 8:1 to 12:1, and the amount of air should be limited to prevent excessive temperatures of combustion and thermal runaway. It is not necessary to strictly maintain the overall mass flow rate constant if the flow rates of the air and gases are measured independently.

Where the reference gas is introduced at sufficiently frequent intervals to assure that humidity has not changed, normal air can be used as the combustion supporting gas. If the reference gas is not introduced at such sufficiently frequent intervals, then the air is preferably dried to a very low humidity, such as less than 5% relative humidity.

A maximum temperature of oxidation, $T_{ref}$, is sensed by microcontroller 18 from sensor 20 to establish the molar flow rate, $\dot{n}_{ref}$. Instead of sensing a maximum temperature of combustion, this point can also be located by inference. The mixture of air and fuel is varied to obtain two points of equal temperature on either side of a maximum temperature and corresponding to different flow rates.

Next, valve 13 is closed and valve 12 is opened. Sample gas flows through apparatus 15, 16, is mixed in apparatus 17 and the mixture flows into the catalytic apparatus 19. The ratio of gases in the second mixture of air and sample gas is regulated until the temperature of the catalytic combustion is at a substantially maximum temperature.

A maximum temperature of oxidation, $TEMP_{MAX}$ is sensed by microcontroller 18 from signals from sensor 20 to establish a molar flow rate, $\dot{n}_{sample}$, for the sample gas. The heating value of the reference gas, $H_{ref}$, is a predetermined value stored in memory for access by the microcontroller. From the molar flow rates and this number, the heating value of the sample gas, $H_{sample}$, can be calculated according to equation (1) above. The measurement of the molar flow rates is proportional to measuring fuel-to-air ratios of the reference and sample gas. If the flows of air in each ratio are the same, or if adjustments are made for any difference in air flows, the ratio reduces to the ratio of flow of the sample gas to the flow of the reference gas.

The catalytic bed 19 is composed of material which will promote and enhance oxidation of the gas without flame combustion, and is usually formed of platinum and/or palladium coated on a fibrous material. The heater 21 is located at or in the catalyst bed to provide an initial starting temperature for the reaction. The temperature sensor 20 provides a signal proportional to the temperature at the reaction surface of the catalytic material.

The temperature of the combustion can be controlled by diffusion processes or by mechanical heat sinks so as to prevent thermal runaway. The catalytic apparatus 19 can be constructed to include diffusion beads or pellisters.

Pellisters have been manufactured for a long period and are used in gas detectors for mines and various other confined and hazardous location instruments. They are constructed by diffusing the catalyst into the pores of a ceramic bead on a wire. The pellister, therefore, provides a temperature limiting since the mixed gas must diffuse into the ceramic pores to react with the catalyst. The pellister has a limited reaction rate. The pellister can be mounted in a stream of mixed gas and will not overheat or runaway if the flow rate past the pellister is limited and does not interfere with the diffusion process.

In another construction of the catalytic apparatus 19, a sintered metal plate or ball is coated on a small section with the catalyst, and the metal plate or ball is connected to a suitable heat sink. The fuel/air mixture is then directed to flow through the sintered material, where it is oxidized. The products of stoichiometric combustion have insufficient heat capacity to control and limit temperature of the oxidation, and a mechanical heat sink is added for this purpose. The sintered metal plate or ball heats up to a certain temperature during the flow of the reference gas and maintains this same temperature during the flow of the sample gas.

A third way to construct the catalytic apparatus 19 utilizes wires coated with catalytic material and arranged radially like the spokes of a wheel inside a ring-shaped heat sink.

During catalytic combustion, flow rate control must be exercised to limit the heat generation by controlling catalyst temperature. For example, the total flows of the first and second mixtures are limited to limit catalyst temperature. Preferably, the reaction is carried out in an ambient atmosphere at a temperature in a range from approximately −40° F. to approximately 130° F.

Figure 2A:
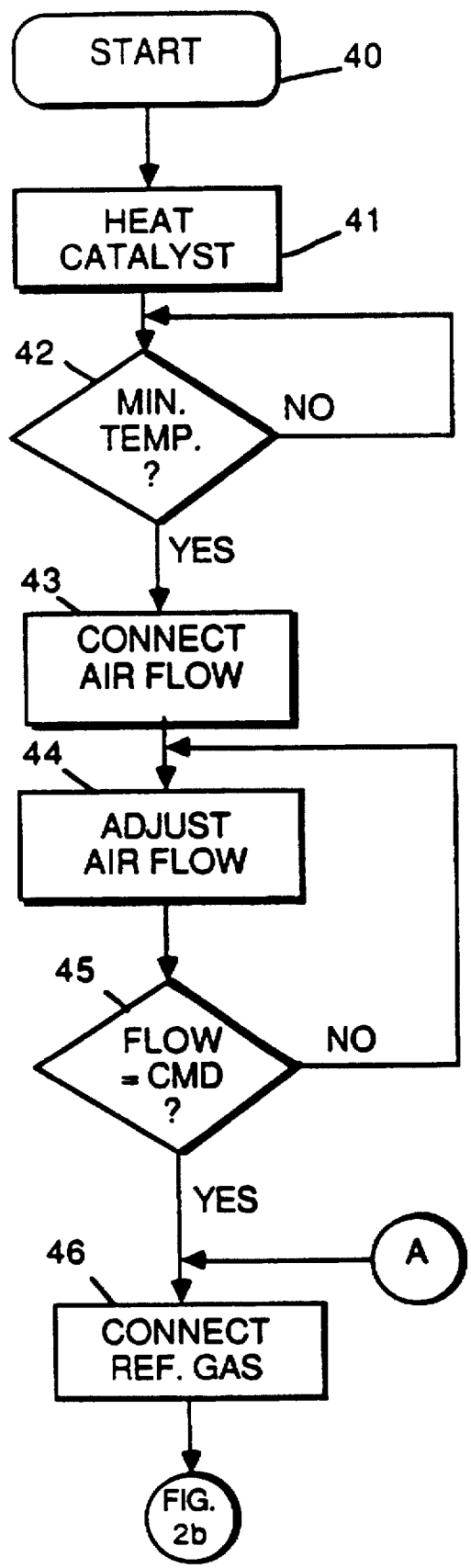
FIGS. 2a and 2b are flow charts of the method of the present invention as performed by the apparatus of FIG. 1.

FIG. 2a illustrates operation of the apparatus of the invention. Block 40 represents the start of microcontroller operations related to the invention. These operations are carried out by the microcontroller 18, by executing program instructions in a program stored in a memory. As represented by block 41, the microcontroller 18 first turns on heater 21 to heat the catalytic device. It then senses temperature through sensor 20 and executes instructions represented by decision block 42 to see if a minimum operating temperature has been reached. It loops back to re-execute block 42 until the minimum operating temperature has been reached.

The microcontroller 18 then proceeds to execute instructions represented by process block 43 to turn on valve 11 to start the flow of air. Next, the microcontroller 18 transmits an air flow command to flow rate control 14 as represented by process block 44. The microcontroller 18 then executes instructions represented by decision block 45 to sense the flow of air from flow meter 25. If the commanded air flow is reached, as represented by the "YES" result from block 45, the program proceeds. If not, as represented by the "NO" branch, the microcontroller 18 loops back to execute process block 44 to transmit a new command to flow rate control 14 and continues to test at decision block 45 until the proper air flow rate is reached.

Figure 2B:
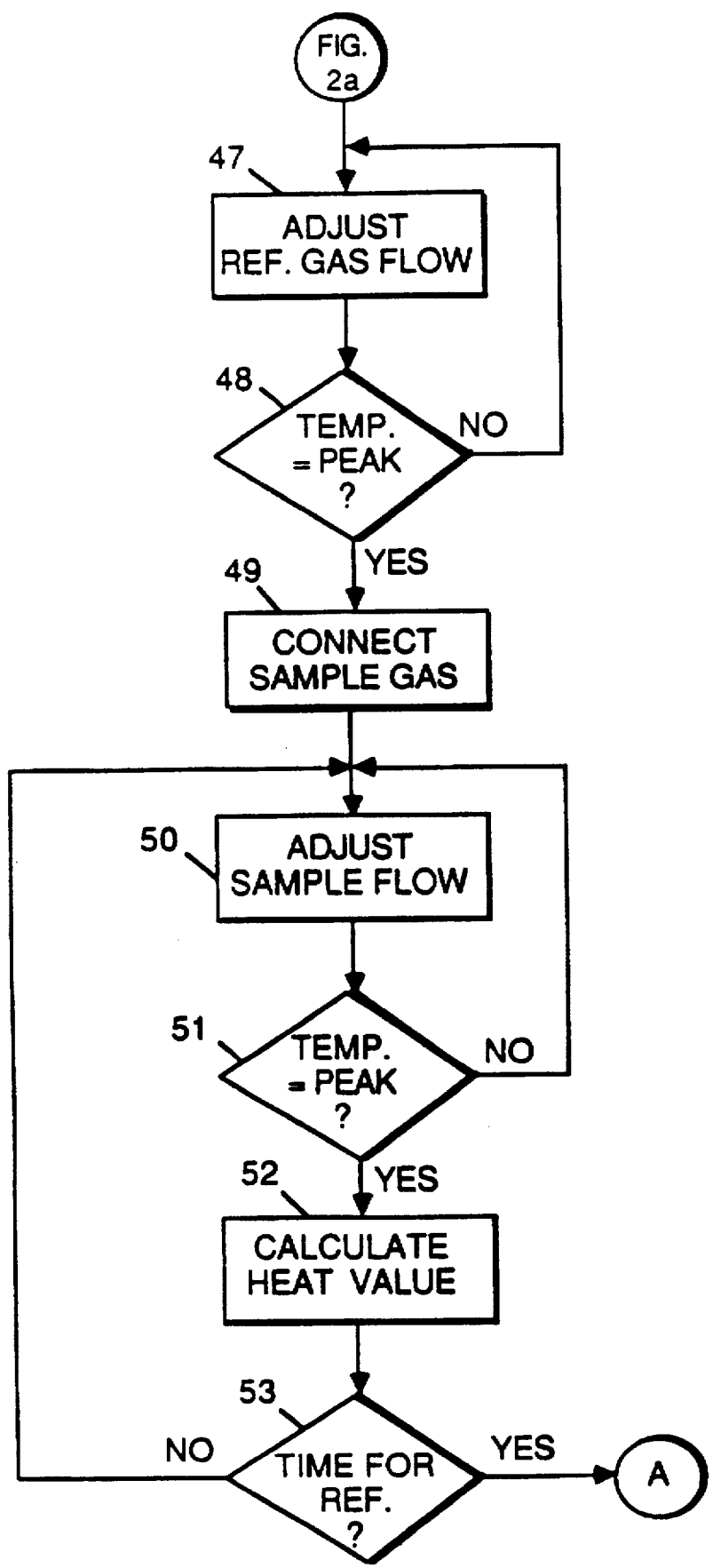

Upon reaching the proper air flow, the microcontroller 18 then proceeds to execute instructions represented by process block 46 to turn on valve 13 to start the flow of the reference gas and transmit a reference gas flow command to flow rate control 15 as represented by process block 47 in FIG. 2b. The microcontroller 18 then executes instructions represented by decision block 48 in FIG. 2b to sense the combustion temperature from sensor 20. If the maximum combustion temperature has not been reached, the microcontroller 18 loops back to process block 47 to transmit a new command to flow rate control 15 and continues to test at decision block 48 until the reference gas flow rate is reached that corresponds to maximum temperature of combustion.

Next, as represented by process block 49, valve 13 is closed and valve 12 is opened to admit the sample gas 12, and the flow is adjusted as represented by process block 50. The microcontroller 18 then executes instructions represented by decision block 51 to sense the combustion temperature from sensor 20. If the maximum combustion temperature has not been reached, the microcontroller 18 loops back to process block 50 to transmit a new command to flow rate control 15 and continues to test at decision block 51 until the sample gas flow rate is reached that corresponds to maximum temperature of combustion.

Then, as represented by process block 52, the microcontroller 18 calculates the heating value for sample gas, based on equation (1) above. Data for the heating valve of the reference gas has been pre-stored in memory for this purpose. The heating value of the sample gas, $H_{sample}$ may then be transmitted to a visual display or other output device.

As represented by decision block 53, a timer is checked periodically, so that the reference gas is admitted periodically for a calibration cycle in which the program follows the "YES" branch through the "A" connectors to process block 46 in FIG. 2a. Otherwise, the process continues with cycles of measurement of the sample gas, as represented by the "NO" branch from decision block 53.

Figure 3:
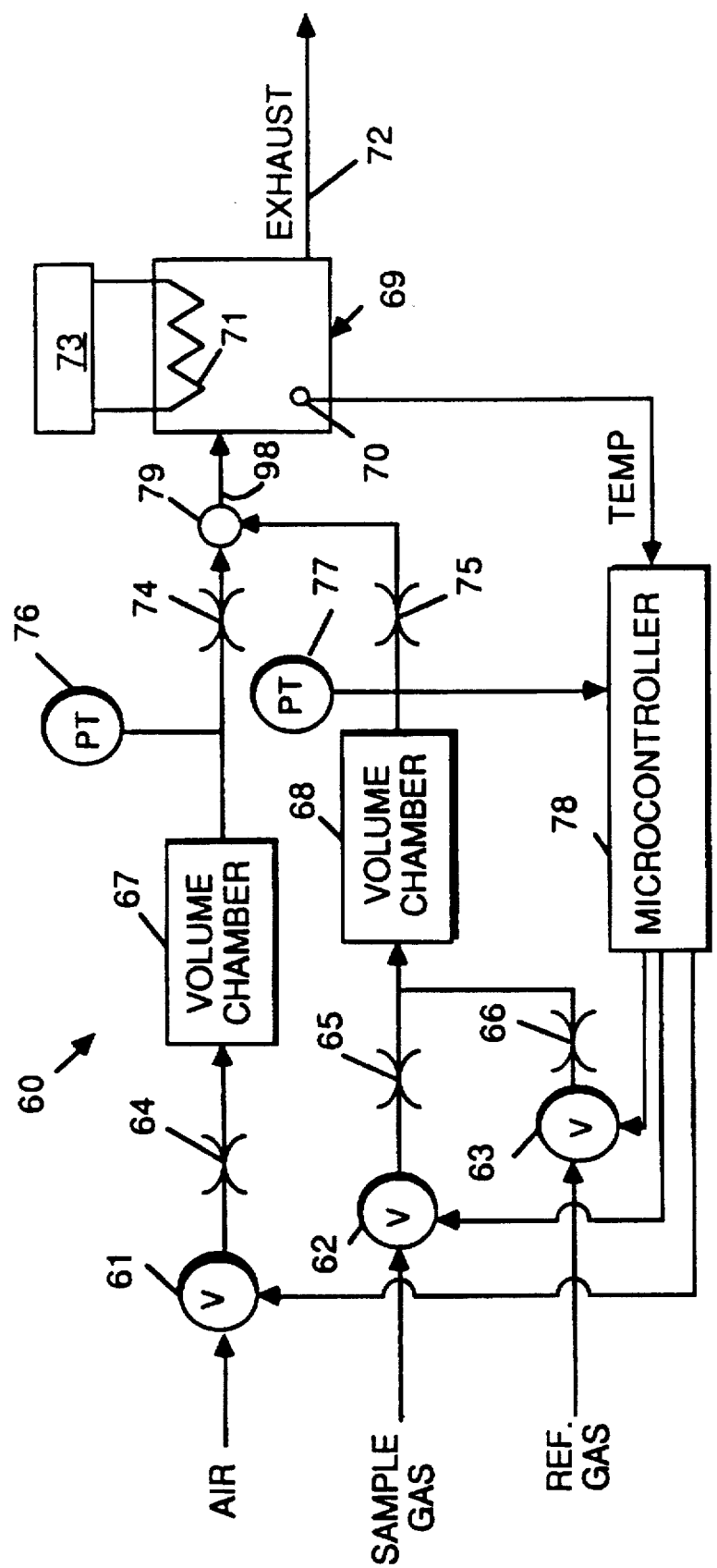
FIG. 3 is a schematic diagram of a second, preferred embodiment of an apparatus for practicing the present invention.

Referring to FIG. 3, a simpler apparatus is presented as the preferred embodiment of the invention. The apparatus is represented generally by reference 60. Catalytic heater apparatus 69 includes heater element 71 for heating the catalytic material to a temperature of 400° C. or more. Heater element 71 is energized by electricity from a power source 73. Temperature sensor 70 is embedded in the catalytic material to sense the temperature at the reaction surface of the catalytic material. Temperature sensor 70 generates a signal representative of temperature to an input on microcontroller 78. Any air or gas remaining after the catalytic reaction is exhausted from catalytic device 69 in an exhaust stream 72.

Microcontroller 78 is a suitable microelectronic CPU (central processing unit) with built-in A-to-D and D-to-A interface circuitry. Microcontroller 78 operates by executing program instructions, some of which are represented by blocks in the flow chart in FIG. 4, the instructions being stored in a memory also represented generally by reference 78.

Apparatus 60 more particularly includes solenoid valve 61 for allowing flow of air through flow restrictor 64 to volume chamber 67. Solenoid valves 62 and 63 control flow of sample gas and reference gas, respectively, through flow restrictors 65, 66, respectively, to volume chamber 68. Whenever the other one of the sample and reference gases is introduced, it is allowed to flow long enough to purge the chamber 68 of the previous gas. Initially, the valves 61, and 62 or 63, are opened to charge the volume chambers 67, 68 to a pressure of 5 psi for example. The valve for the combustible gas, either 62 or 63, is then closed. The flow of gas slowly reduces as the chamber pressure declines, thereby causing the mixture of fuel-to-air to become leaner. In the embodiment in FIG. 3, the air supply valve 61 must be turned on and off at relatively short intervals to maintain a constant air supply during the time that the fuel-to-air mixture is being leaned out. The fuel and air flow through flow restrictors 74, 75 are mixed at junction 79. From there, the fuel and air mixture flows through conduit 98 to catalytic device 69. The temperature of combustion is sensed by temperature sensor 70 which transmits a signal representative of temperature to microcontroller 68.

Pressure transducers 76 and 77 are connected to output flows from volume chambers 67, 68. The method of Kennedy, U.S. Pat. No. 4,285,245 is utilized to measure molar flow rate of the reference gas, $\dot{n}_{ref}$, as a change of pressure with respect to time (dP/dt)(FIG. 5) as gas flows out of volume chamber 68 (FIG. 3). Similarly, the method of Kennedy is then utilized to measure $\dot{n}_{sample}$, the molar flow rate of the sample gas, $\omega_{air\ ref}$, the mass flow rate of air to be mixed with the reference gas flow stream, and $\omega_{air\ sample}$ the mass flow rate of air to be mixed with the sample gas flow stream.

Thus, the microcontroller 68 can calculate $H_{sample}$, the heating value of the sample gas, according to Equation (1) above, provided the heating value of the reference gas, $H_{ref}$, has been pre-stored in memory and is available for the calculation. Again, either air of less than 5% relative humidity can be used, or the process can be repeated at intervals which minimize or eliminate humidity factors and barometric changes.

Figure 5:
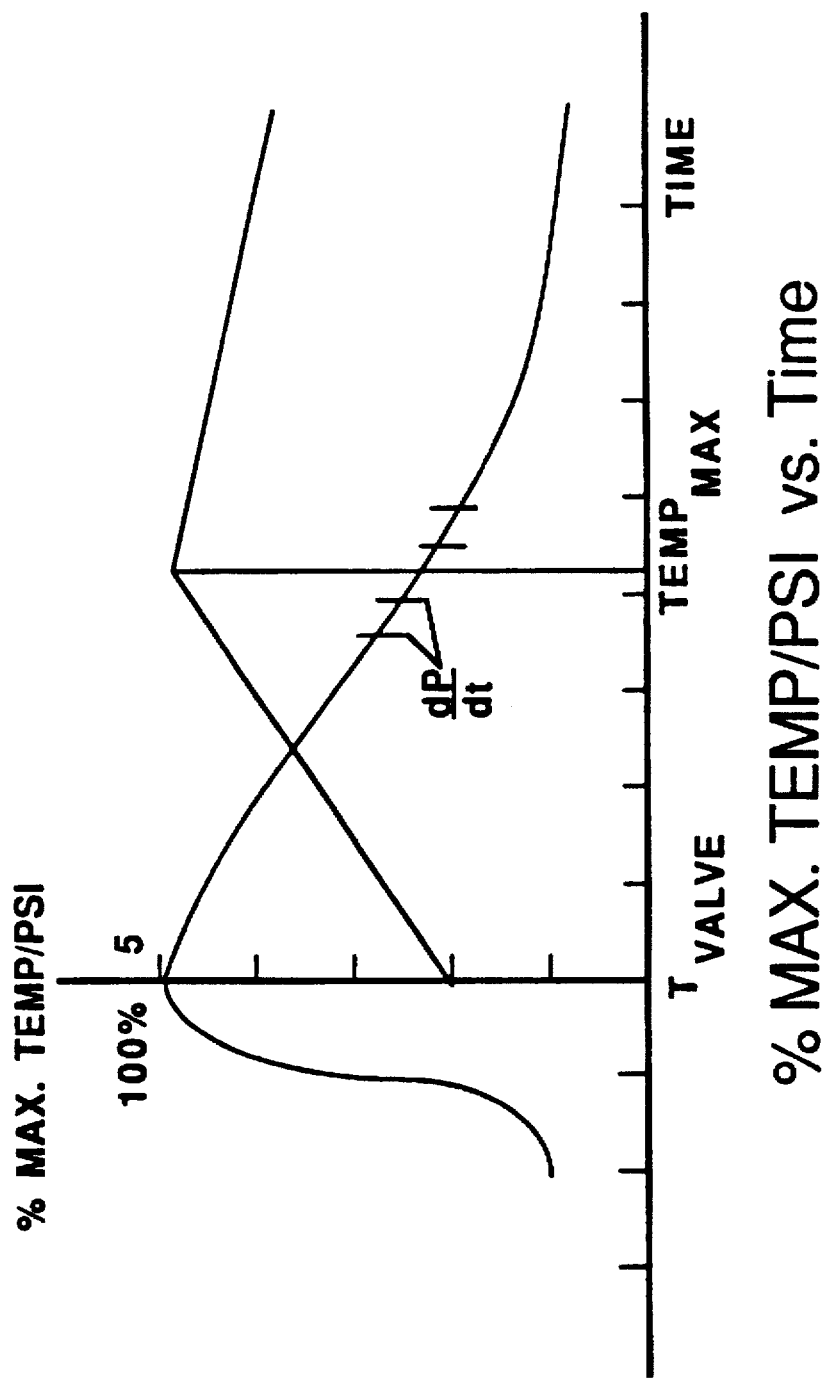
FIG. 5 is a graph illustrating operation of the apparatus of FIG. 3.

FIG. 5 illustrates the operation of the apparatus of FIG. 3 with a graph of per cent maximum temperature of the catalyst vs. time, and a graph of pressure vs. time for volume chamber 68. At some time before valve 62 or 63 is closed, chamber 68 is charged to some pressure, e.g. 5 psi, as shown in FIG. 5. At time t=0, the valve 62 or 63 is closed, and pressure decays over time. At first, a rich fuel-to-air mixture is provided to the catalyst, but as pressure decays, the mixture becomes leaner until a maximum catalyst temperature, $TEMP_{MAX}$ is reached at some corresponding time, t, and then the temperature of combustion declines as the mixture becomes very lean.

The preferred sensors 20 and 70 have been shown and described as temperature sensors. However, it should be appreciated that substantially maximum catalytic combustion can also be sensed with oxygen detectors, which sense the oxygen remaining in the exhaust stream. When oxygen is at a minimum, combustion is substantially complete and the fuel-to-air ratio is at an optimum mixture for oxidation of the combustible gas.

Figure 4A:
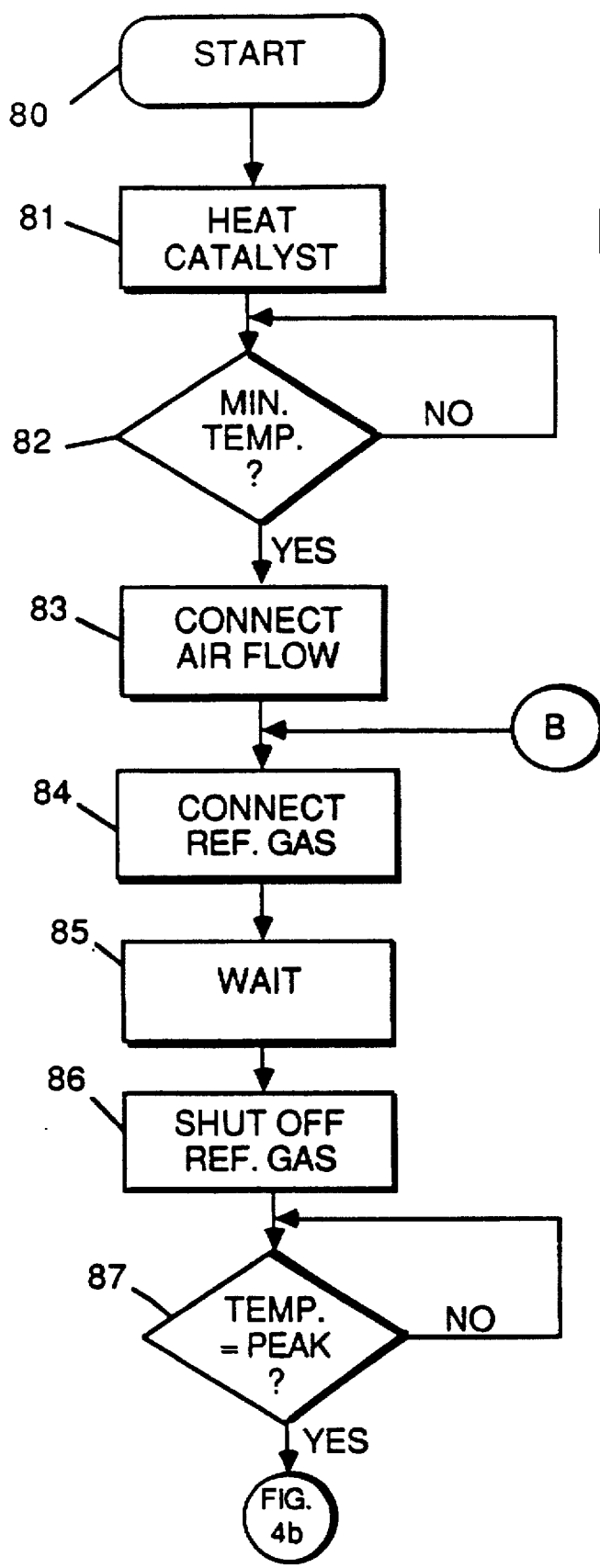
FIGS. 4a and 4b are flow charts of the method of the present invention as performed by the apparatus of FIG. 3.
Figure 4B:
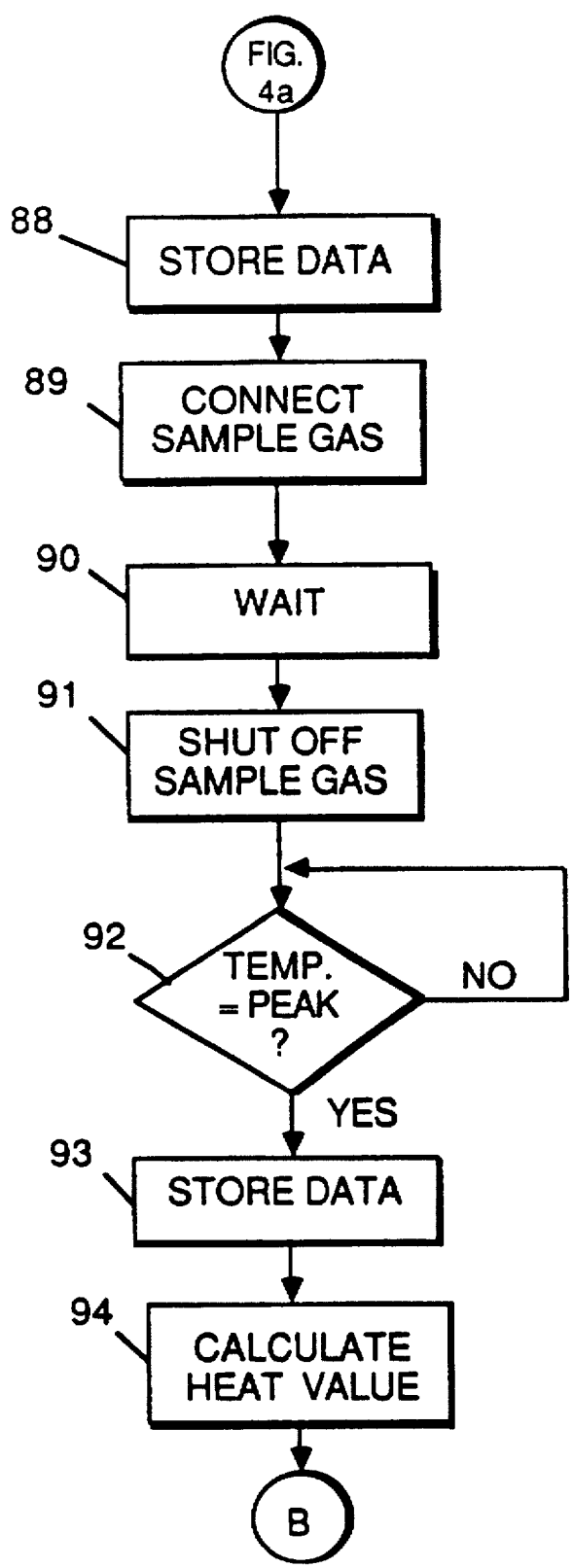

FIGS. 4a and 4b illustrate operation of the apparatus of FIG. 3. These operations are carried out by the microcontroller 78, by executing program instructions in a program stored in a memory within microcontroller 18. Block 80 represents the start of a portion of the microcontroller program. As represented by block 81, the microcontroller 78 first turns on heater 71 to heat the catalytic device 69. It then senses temperature through sensor 70 and executes instructions represented by decision block 82 to see if a minimum operating temperature has been reached. It loops back to re-execute block 82 until the minimum operating temperature has been reached.

The microcontroller 78 then executes instructions represented by process block 83 to open valve 61 to start the flow of air. Next, the microcontroller 18 executes instructions represented by process block 84 to open valve 63 to start the flow of reference gas. The microcontroller 78 then executes instructions represented by decision block 85 to wait until the pressure of reference gas in volume chamber 68 has reached some predetermined level such as 5 psi.

Upon reaching the proper pressure, the microcontroller 18 then executes instructions represented by process block 86 to close valve 63 and shut off the supply of reference gas. Reference gas continues to flow out of volume chamber 68, which causes a drop in pressure in the chamber. The microcontroller 78 then executes instructions represented by decision block 87 to monitor the time when the temperature of combustion has passed through a peak. As represented by process block 88 in FIG. 4b, the microcontroller 78 will read temperature data from sensor 70 over a period of time and will also read pressure data from pressure transducers 76, 77, so that it can store the flow rates corresponding to maximum temperature. The microcontroller 78 will then proceed to execute instructions in the next part of the program represented by process block 89.

Next, as represented by process block 89, valve 63 is closed and valve 62 is opened to admit the sample gas to volume chamber 68. The microcontroller 78 then executes instructions represented by block 90 to wait and allow volume chamber 68 to be purged of the reference gas and replaced with the sample gas at 5 psi.

Upon reaching the proper pressure, the microcontroller 78 then executes instructions represented by process block 91 to close valve 62 and shut off the flow of sample gas. Sample gas flows out of volume chamber 68 and pressure drops, as illustrated in FIG. 5. The microcontroller 78 then executes instructions represented by decision block 92 to detect whether the temperature of combustion has passed through a peak. As represented by process block 93 in FIG. 4b, the microcontroller 78 will read temperature data from sensor 70 over a period of time and will also read pressure data from pressure transducers 76, 77, so that it can calculate and store the air and fuel flow rates corresponding to maximum temperature.

The microcontroller 78 will then proceed to execute instructions represented by process block 94 to calculate the heat value based on equation (1) above and based on the flow rates for sample gas and reference gas at the maximum temperature of catalytic combustion. Data for the heating value of the reference gas, $H_{ref}$, has been pre-stored in memory for calculating the heating value of the sample gas, $H_{sample}$, according to equation (1) above. Air flow rates can also be used in the calculation, if necessary, where the air flow rate is different in the mixtures of sample gas and reference gas, respectively. After calculation, the heating value of the sample gas, $H_{sample}$, may then be transmitted to a visual display or other output device. The program then returns through connector B to execute another cycle for the reference gas.

The apparatus of FIG. 3 includes simplified flow components for providing a sample flow of the sample gas and the reference gas. This provides an apparatus that is lower in cost and smaller in size than other possible apparatus for practicing the methods of the invention.

This has been a description of examples of how the invention can be carried out. Those of ordinary skill in the art will recognize that various details may be modified in arriving at other detailed embodiments, and these embodiments will come within the scope of the invention.

Therefore, to apprise the public of the scope of the invention and the embodiments covered by the invention, the following claims are made.

We claim:

1. A method of measuring heating value of a combustible gas that is combusted through substantially stoichiometric combustion, the method comprising:

flowing a mixture of a reference gas and a combustion supporting gas into a catalytic combustion device to cause flameless combustion of the reference gas;

sensing combustion temperature in the catalytic combustion device;

varying a mixture ratio of the reference gas to the combustion supporting gas to obtain substantially stoichiometric combustion at about a maximum combustion temperature;

flowing a mixture of a sample gas and a combustion supporting gas into the catalytic combustion device to cause flameless combustion of the sample gas;

varying a mixture ratio of the sample gas to the combustion supporting gas to obtain to obtain substantially stoichiometric combustion at about a maximum combustion temperature; and wherein the mixture ratio of the reference gas to the combustion supporting gas and the mixture ratio of the sample gas to the combustion supporting gas are each varied by capturing a volume of the reference gas and the sample gas, respectively, in a chamber and releasing the reference gas and the sample gas, respectively, to flow out of the chamber as pressure in the chamber decays; and calculating the heating value of the sample gas in response to changes in pressure in the chamber with respect to time and with respect to temperature measurements at about the maximum temperature of catalytic combustion corresponding to substantially stoichiometric combustion for the reference gas and the sample gas, respectively.

2. The method of claim 1, wherein the temperature measurements at about the maximum temperature of catalytic combustion are sensed by varying at least one of said mixture ratios and sensing temperature until points of equal temperature are sensed, before and after said maximum temperature, for different values of said one of said mixture ratios.

3. The method of claim 1, wherein the step of varying the reference gas mixture ratio and the step of varying the sample gas mixture ratio further comprises regulating the supply of at least one of said gases in at least one of said mixture ratios until the temperature of combustion is at a substantially maximum temperature.

4. The method of claim 1, wherein the step of varying the reference gas mixture ratio and the step of varying the sample gas mixture ratio further comprises regulating the supply of the combustion supporting gas in at least one of said mixture ratios.

5. The method of claim 1, wherein the supply of combustion supporting gas in the reference gas flow is equal to the supply of combustion supporting gas in the sample gas flow.

6. The method of claim 1, further comprising the step of separately metering a flow of said combustion supporting gas from the flow of reference gas and the flow of sample gas.

7. The method of claim 1, wherein said method is performed at ambient temperatures of from approximately –40° F. to 130° F.

8. The method of claim 1, wherein the combustion supporting gas is air.

9. The method of claim 8, wherein the air is of less than 5% relative humidity.

10. An apparatus for determining the heating value of a combustible gas that is combusted through substantially stoichiometric combustion, the apparatus comprising:

first means for establishing flow of a combustion supporting gas;

second means for establishing flow of a combustible gas by capturing a volume of said combustible gas in a chamber and then releasing the combustible gas to flow out of said chamber as pressure in the chamber decays;

means for sensing changes of pressure in the chamber;

means for conducting a mixture of said combustible gas and said combustion supporting gas into a catalytic combustion device;

means for selectively flowing either a reference combustible gas or a sample combustible gas to said second means for establishing flow of said combustible gas;

means for sensing combustion temperature in the catalytic combustion device;

a control means for receiving signals from said means for sensing combustion temperature and from said means for sensing pressure changes in the chamber, said control means further comprising:

first control means for repeatedly determining temperature in the catalytic combustion device up to about a maximum temperature of catalytic combustion;

second control means for repeatedly detecting pressure changes corresponding to flow rates of said reference combustible gas and said sample combustible gas, respectively, up to about the maximum temperature of catalytic combustion for each respective combustible gas; and third control means for calculating the heating value of said sample combustible gas in response to a heating value for a reference combustible gas and in response to flow rates for the reference combustible gas and a sample combustible gas, respectively, at the about the maximum temperature of combustion, wherein said flow rates are determined in response to said pressure changes.

11. The apparatus of claim 10, wherein said second means for establishing controlled flow of the combustible gas includes means for transmitting a command for the flow of said combustible gas, and means responsive to said second means for sensing, for varying the command for the flow of said combustible gas, thereby providing closed loop control.

12. The apparatus of claim 10, wherein said second control means determines a substantially maximum temperature of catalytic combustion by sensing pressure changes for points of substantially equal temperature occurring before and after said substantially maximum temperature of catalytic combustion.

13. The apparatus of claim 10, wherein said means for conducting a mixture of said combustible gas and said combustion supporting gas into the catalytic combustion device includes a sintered metal ball for maintaining a stable, non-varying temperature condition for the reference gas and the sample gas.

14. The apparatus of claim 10, wherein said first means for establishing flow of the combustion supporting gas is controlled separately from said second means for establishing controlled flow of the combustible gas.

15. The apparatus of claim 14, wherein said means for separately controlling the flow of said combustible gas includes a molar flow meter.

16. The apparatus of claim 15, wherein said combustion supporting gas is air.

17. The apparatus of claim 16, wherein the combustion supporting gas is air at less than 5% relative humidity.

18. A method of measuring heating value of a combustible gas that is combusted through substantially stoichiometric combustion, the method comprising:

flowing a mixture of a reference gas and a combustion supporting gas into a catalytic combustion device to cause flameless combustion of the reference gas;

sensing combustion temperature in the catalytic combustion device;

varying flow rate of the reference gas to obtain stoichiometric combustion at about a maximum combustion temperature;

flowing a mixture of a sample gas and a combustion supporting gas into the catalytic combustion device to cause flameless combustion of the sample gas;

varying flow rate of the sample gas to obtain to obtain stoichiometric combustion at about a maximum combustion temperature; and calculating the heating value of the sample gas in response to changes in flow rates of the reference gas and the sample gas, respectively, and with respect to temperature measurements at about a maximum temperature of catalytic combustion for the reference gas and the sample gas, respectively.

19. The method of claim 18, wherein the temperature measurements at about the maximum temperature of catalytic combustion are sensed by varying the flow rates of the reference gas and the sample gas, respectively, and sensing temperature until two points of equal temperature of combustion are sensed for different flow rates for each respective gas.

20. An apparatus for determining the heating value of a combustible gas that is combusted at substantially stoichiometric combustion, the apparatus comprising:

first means for establishing flow of a combustion supporting gas;

second means for causing a variable flow rate of a combustible gas;

means for sensing flow rate;

means for conducting a mixture of said combustible gas and said combustion supporting gas into a catalytic combustion device;

means for selectively flowing either a reference combustible gas or a sample combustible gas to said second means for causing a variable flow rate of the combustible gas;

means for sensing combustion temperature in the catalytic combustion device;

a control means for receiving signals from said means for sensing combustion temperature and from said means for sensing flow rate of the combustible gas, said control means further comprising:

first control means for repeatedly determining temperature in the catalytic combustion device up to about a maximum temperature of catalytic combustion;

second control means for detecting flow rates of said reference combustible gas and said sample combustible gas, respectively, up to about the maximum temperature of catalytic combustion; and third control means for calculating the heating value of said sample combustible gas in response to a heating value for a reference combustible gas and in response to flow rates for the reference combustible gas and a sample combustible gas, respectively, at about the maximum temperature of catalytic combustion.

21. The apparatus of claim 20, wherein said second control means detects a substantially maximum temperature of combustion by detecting flow rates for points of substantially equal temperature of combustion occurring before and after said substantially maximum temperature.

* * * * *

UNITED STATES PATENT AND TRADEMARK OFFICE
CERTIFICATE OF CORRECTION

Patent No.   : 5,759,862

Dated        : June 2, 1998

Inventor(s)  : Vander Heyden, et al.

It is certified that error appears in the above-identified patent and that said Letters Patent is hereby corrected as shown below:

Column 2, line 59, "is a accomplished" should be --is accomplished--.

Column 9, line 59, "to obtain to obtain" should be --to obtain--.

Column 12, line 1, "to obtain to obtain" should be --to obtain--.

Signed and Sealed this

Fifteenth Day of December, 1998

Attest:

BRUCE LEHMAN

*Attesting Officer*     *Commissioner of Patents and Trademarks*